(12) United States Patent
Baumgart et al.

(10) Patent No.: US 11,723,619 B2
(45) Date of Patent: Aug. 15, 2023

(54) SYSTEM AND METHOD FOR INDICATION AND SELECTION OF REGION OF INTEREST FOR X-RAY DOSE ADJUSTMENT

(71) Applicant: CANON MEDICAL SYSTEMS CORPORATION, Otawara (JP)

(72) Inventors: John Baumgart, Vernon Hills, IL (US); Joseph Manak, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 56 days.

(21) Appl. No.: 17/206,866

(22) Filed: Mar. 19, 2021

(65) Prior Publication Data

US 2022/0296197 A1 Sep. 22, 2022

(51) Int. Cl.
*A61B 6/00* (2006.01)
*G06N 20/00* (2019.01)

(52) U.S. Cl.
CPC .............. *A61B 6/542* (2013.01); *A61B 6/465* (2013.01); *A61B 6/469* (2013.01); *A61B 6/58* (2013.01); *G06N 20/00* (2019.01); *A61B 2560/0493* (2013.01)

(58) Field of Classification Search
CPC ......... A61B 6/542; A61B 6/465; A61B 6/469; A61B 6/58; A61B 2560/0493; G06N 20/00
See application file for complete search history.

(56) References Cited

U.S. PATENT DOCUMENTS

| 6,990,171 | B2 | 1/2006 | Toth et al. |
| 7,725,163 | B2 | 5/2010 | Schmitz et al. |
| 2012/0014586 | A1 | 1/2012 | Kosarev |
| 2016/0157812 | A1 | 6/2016 | Jung et al. |
| 2018/0338742 | A1 | 11/2018 | Singh et al. |
| 2020/0387729 | A1* | 12/2020 | Ichinose ............ G06T 7/11 |
| 2022/0207795 | A1* | 6/2022 | Brown ............ A61B 6/545 |

FOREIGN PATENT DOCUMENTS

CN 110811663 A 2/2020

OTHER PUBLICATIONS

Extended European Search Report dated Aug. 4, 2022 in European Patent Application No. 22163025.4, 10 pages.
Deshpande et al., "Deep Learning Based Segmentation of Body Parts in CT Localizers and Application to Scan Planning", 2020 IEEE 17th International Symposium on Biomedical Imaging (ISBI), IEEE, Apr. 3-7, 2020, Iowa City, Iowa, USA, pp. 1130-1133, XP033774163.

* cited by examiner

*Primary Examiner* — Jurie Yun
(74) *Attorney, Agent, or Firm* — Oblon, McClelland, Maier & Neustadt, L.L.P.

(57) ABSTRACT

A system and a method by which multiple regions or objects of interest can be indicated within an X-ray image, from which a user can select a primary region or object of interest and accordingly adjust the appropriate X-ray dose for obtaining a better quality image of the selected regions or objects of interest.

24 Claims, 6 Drawing Sheets

SYSTEM AND METHOD FOR INDICATION AND SELECTION OF REGION OF INTEREST FOR X-RAY DOSE ADJUSTMENT

TECHNICAL FIELD

The disclosure relates to adjusting x-ray dosage in x-ray imaging.

BACKGROUND

In an x-ray image, there may be several objects that are of interest to a user at a given time, including anatomic markers or features, implanted devices, and interventional devices. The visibility of any of these is dependent on optimizing the x-ray dose to the patient for that object, which may compromise the visibility of other objects seen in the image. If it is not known what the primary object of interest is, it is possible that the x-ray dose is either too low or higher than is necessary to sufficiently resolve the particular object in an image.

Current practice relies on an overall or weighted regional measurement of an acquired image to determine the proper x-ray dose, but this disregards what a user is interested in seeing within an image with respect to the actual image content. In addition, current practice uses fixed regions of interest that may or may not have anything to do with patient anatomy or objects of interest therein. In general, in a section of a human body whose an x-ray image has been taken, there are several smaller sections mingled with other smaller sections, each of the various sections having intensity level different than the neighboring sections. A selected x-ray dose may not be the proper one for displaying the particular section a user wants to see in a high quality image.

SUMMARY

This application presents a system and a method by which multiple regions or objects of interest can be indicated within an x-ray image, from which a user can select a primary region or object of interest. Identifying such regions or objects is done by the system with the assistance of, for example, a neural network. After the regions or objects are identified, the system provides the user the choice of a desired region or objects and sets the appropriate x-ray dose for the selected region or objects.

BRIEF DESCRIPTION OF THE DRAWINGS

The application will be better understood in light of the description which is given in a non-limiting manner, accompanied by the attached drawings in which.

DETAILED DESCRIPTION OF THE PREFERRED EMBODIMENTS

Reference throughout this specification to "one embodiment" or "an embodiment" means that a particular feature, structure, material, or characteristic described in connection with the embodiment is included in at least one embodiment of the application, but do not denote that they are present in every embodiment.

Thus, the appearances of the phrases "in one embodiment" or "in an embodiment" in various places throughout this specification are not necessarily referring to the same embodiment of the application. Furthermore, the particular features, structures, materials, or characteristics may be combined in any suitable manner in one or more embodiments.

The operating environment of the present embodiments is described with respect to a computed tomography (CT) system. Moreover, the present embodiments will be described with respect to the detection and conversion of x-rays. However, one skilled in the art will further appreciate that the present embodiments are equally applicable for the detection and conversion of other high frequency electromagnetic energy, and also equally applicable with a wide variety of CT systems. That is, it is contemplated that the present embodiments may be utilized with energy integrating, photon counting (PC), and/or photon energy discriminating (ED) CT detector systems.

Figure 1:
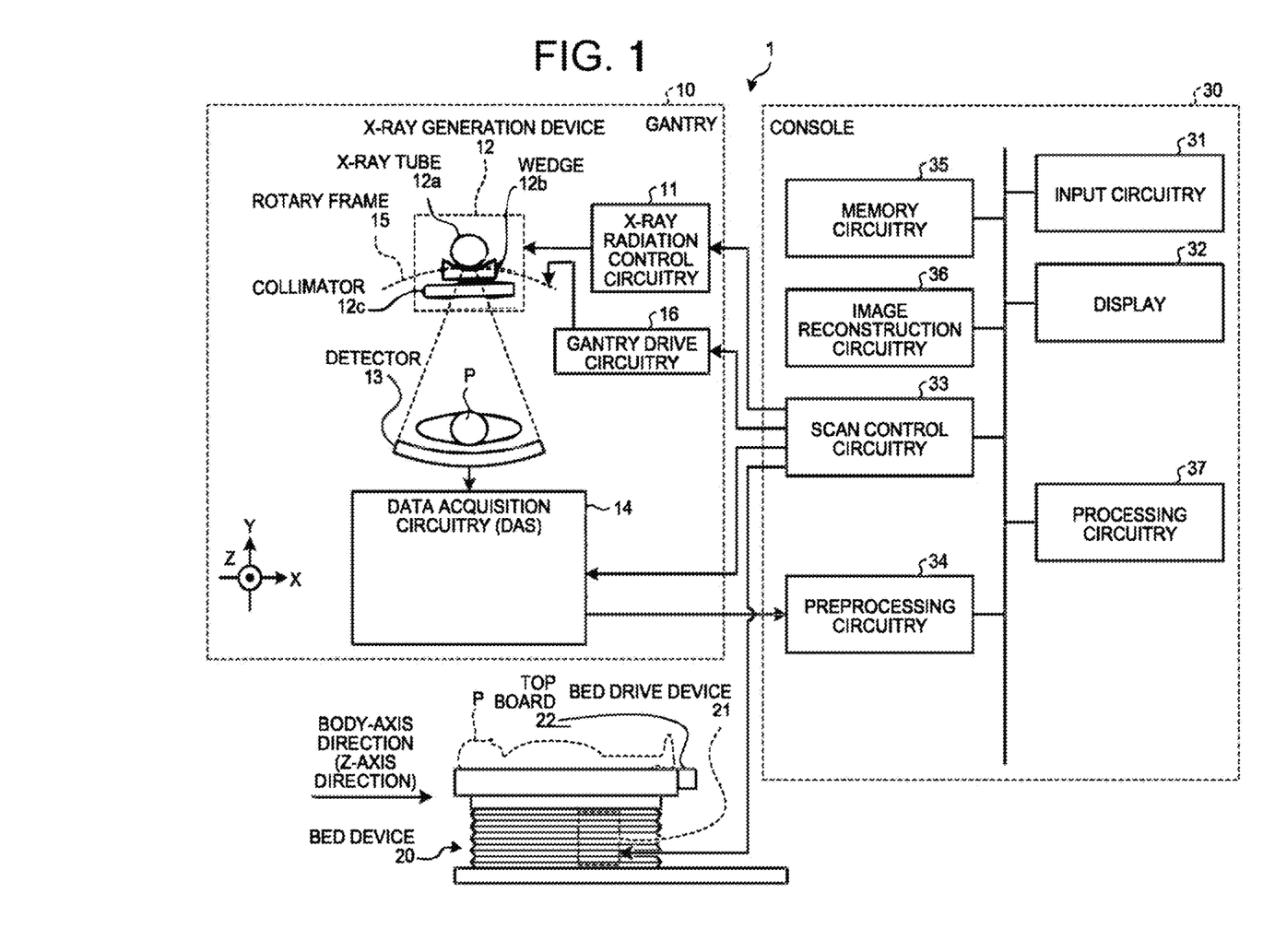
FIG. 1 shows an example of the configuration of a photon-counting type X-ray CT apparatus.

FIG. 1 is a diagram that illustrates an example of the configuration of a photon-counting type X-ray CT apparatus 1. As illustrated in FIG. 1, the photon-counting type X-ray CT apparatus 1 includes a gantry 10, a bed device 20, and a console 30.

The gantry 10 is a device that emits X-rays to a subject P (patient), detects the X-rays that are transmitted through the subject P, and outputs them to the console 30, and it includes X-ray radiation control circuitry 11, an X-ray generation device 12, a detector 13, data acquisition circuitry (DAS: Data Acquisition System) 14, a rotary frame 15, and gantry drive circuitry 16.

The rotary frame 15 is an annular frame that supports the X-ray generation device 12 and the detector 13 such that they are opposed to each other with the subject P interposed therebetween and that is rotated at high speed in a circular orbit around the subject P by the gantry drive circuitry 16.

The X-ray radiation control circuitry 11 is a device that serves as a high-voltage generation unit and supplies a high voltage to an X-ray tube 12a, and the X-ray tube 12a generates X-rays by using the high voltage that is supplied from the X-ray radiation control circuitry 11. Under the control of scan control circuitry 33, the X-ray radiation control circuitry 11 adjusts the tube voltage or the tube current that is supplied to the X-ray tube 12a, thereby adjusting the amount of X-rays that are emitted to the subject P.

Furthermore, the X-ray radiation control circuitry 11 switches a wedge 12b. Furthermore, the X-ray radiation control circuitry 11 adjusts the numerical aperture of a collimator 12c, thereby adjusting the radiation range (the fan angle or the cone angle) of X-rays. Moreover, there may be a case where multiple types of wedges are manually switched by an operator.

The X-ray generation device 12 is a device that generates X-rays and emits the generated X-rays to the subject P, and it includes the X-ray tube 12a, the wedge 12b, and the collimator 12c.

The X-ray tube 12a is a vacuum tube that emits X-ray beams to the subject P by using the high voltage that is supplied by the X-ray radiation control circuitry 11, and it emits X-ray beams to the subject P in accordance with the rotation of the rotary frame 15. The X-ray tube 12a generates X-ray beams that spread with the fan angle and the cone angle. For example, under the control of the X-ray radiation control circuitry 11, the X-ray tube 12a is capable of continuously emitting X-rays all around the subject P for a full reconstruction or continuously emitting X-rays for a half reconstruction within an emission range (180°+the fan angle) that enables a half reconstruction. Furthermore, under the control of the X-ray radiation control circuitry 11, the X-ray tube 12a is capable of intermittently emitting X rays (pulse X-rays) at a previously set position (tube position). Furthermore, the X-ray radiation control circuitry 11 is capable of changing the intensity of X-rays, emitted from the X-ray tube 12a. For example, the X-ray radiation control circuitry 11 increases the intensity of X-rays, emitted from the X-ray tube 12a, at a specific tube position, and it decreases the intensity of X-rays, emitted from the X-ray tube 12a, in the area other than the specific tube position.

The wedge 12b is an X-ray filter that adjusts the amount of X-rays with regard to the X-rays that are emitted from the X-ray tube 12a. Specifically, the wedge 12b is a filter that transmits and attenuates X-rays, emitted from the X-ray tube 12a, such that X-rays, emitted from the X-ray tube 12a to the subject P, has a predetermined distribution. For example, the wedge 12b is a filter that is obtained by processing aluminum so as to have a predetermined target angle or a predetermined thickness. Furthermore, the wedge is also called a wedge filter or a bow-tie filter.

The collimator 12c is a slit that narrows the irradiation range of X-rays, of which the amount of X-rays has been adjusted by the wedge 12b, under the control of the X-ray radiation control circuitry 11.

The gantry drive circuitry 16 drives and rotates the rotary frame 15 so that the X-ray generation device 12 and the detector 13 are rotated in a circular orbit around the subject P.

Each time an X-ray photon enters, the detector 13 outputs the signal with which the energy value of the X-ray photon may be measured. The X-ray photon is, for example, an X-ray photon that is emitted from the X-ray tube 12a and is transmitted through the subject P. The detector 13 includes multiple detection elements that output an electric signal (analog signal) of 1 pulse each time an X-ray photon enters. The photon-counting type X-ray CT apparatus 1 counts the number of electric signals (pulses) so as to count the number of X-ray photons that enter each of the detection elements. Furthermore, the photon-counting type X-ray CT apparatus 1 performs arithmetic processing on the signal so as to measure the energy value of the X-ray photon that causes output of the signal.

In one embodiment, a user is presented with information regarding image content that is used to influence the choice of an x-ray dose. Then, the user is given a feedback mechanism for selecting a primary region of interest (ROI) from those objects detected to be present in the image content information. The selection of an object can then be used to create a new measurement field (i.e., a set of image pixels) that will be considered for setting the dose adjustment.

In one embodiment, a list of objects of interest may be created from an object detection, localization, segmentation, or tracking process (which may include a neural network, or a "You Only Look Once" (YOLO) process, which is one of deep learning-based approaches in object detection).

In object detection, objects are identified in an image or video sequence. Objects can even be recognized when they are partially obstructed from view. This task is still a challenge for computer vision systems. Many approaches to the task can be implemented, including edge detection, appearance-based methods, and feature-based methods. In general, an object detection method falls into either a machine learning-based approach or a deep learning-based approach. Machine learning-based or deep learning-based approaches use trained models which can detect multiple kinds of objects.

In image segmentation, an image is partitioned into multiple regions according to some homogeneity criterion. In medical imaging, these segments often correspond to different tissue classes, organs, pathologies, or other biologically relevant structures. Different approaches have been developed for image segmentation, such as shape-based segmentation, image-based segmentation, interactive segmentation, and subjective surface segmentation.

This list of objects of interest may be presented concurrently with the x-ray image, along with indications as to the object currently being used to establish the measurement field for dose adjustment. The measurement field corresponding with said object is optionally indicated on the image, either temporarily or persistently. The image pixels comprising the measurement field are determined by the detection, localization, segmentation or tracking process. Typically (but not limited), the measurement field is set to include all of the ROI.

A measurement field typically differs from a region of interest. However, even if the measurement field and the region of interest comprise the same image pixels, each pixel of the measurement field may be weighted based on its importance. A pixel in the measurement field may be additionally weighted on how often or how recently it contributed to the measurement field.

An object in an image can be a region or "zone" of the image that has an overall intensity level different from other zones of the image. For example, in a coronary angiogram, one zone could be defined by low intensity levels, containing the spine and diaphragm, while another zone (e.g., the heart) would be defined by medium intensity values, and yet another (e.g., the lung) would be defined by high intensity values. The zone can be a contoured region determined by a machine-learning (ML) process, a bounding box or other stylized region of interest. The zone may be overlaid on the primary image or displayed in a separate graphical representation.

The dimensions of a measurement field may be derived from an ROI based on the existence (or not) of objects in a region of the ROI. The measurement fields may have a wide margin or a small margin depending on the object contained in the measurement field. The size of the margin may be defined either in absolute terms (e.g., millimeters) or relative terms (e.g., with respect to the contained object). Various examples are given below.

A measurement field containing a guide wire would typically have a rather wide margin, as guide wires are very small and tend to be moved around a lot. A large margin would allow such movement without affecting the correct determination of the measurement field.

A measurement field containing a stent would typically have a margin around the stent about the size of the stent itself. Stents typically don't move around within the patient once deployed, so the image information adjacent to the stent won't be unstable.

A measurement field containing a segment of spine would typically have a relatively small margin around the spine, as the spine is stable and is large enough on its own to give a reliably sized measurement field.

A measurement field containing an implanted device (e.g., pacemaker battery, artificial hip, dental work) would typically have little to no margin, as it is typically desired to exclude such a device from influencing dose calculations involving immediately adjacent measurement fields.

In cardiac images where there is periodic motion, a small measurement field around a specific object may move around the image from frame to frame. In this case, the measurement field may be an accumulation of measurement fields from several images to keep the dose stable.

The user is allowed to change the selection of the current primary object of interest using an input device including, but not limited, to a mouse, joystick, jog wheel, touch panel, or voice control. Upon selection of a new primary ROI, the object tracking process is queried for the new measurement field. The new selection is indicated to the user, and the measurement field is then given to the x-ray dose adjustment process to determine the right x-ray dose for the selected new ROI.

Optionally, the user can manually select a ROI. This region can be selected tableside from a still frame or a live sequence displayed on a tablet (the user can use a gesture or ROI selection on the image presented).

Figure 2A:
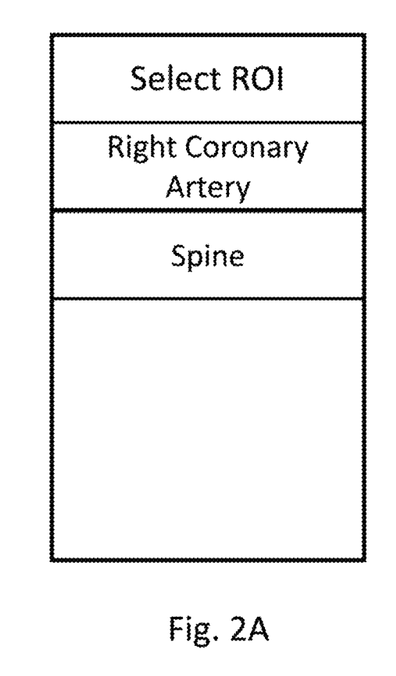
FIGS. 2A, 2B show schematically a selection menu for selecting regions of interest.
Figure 2B:
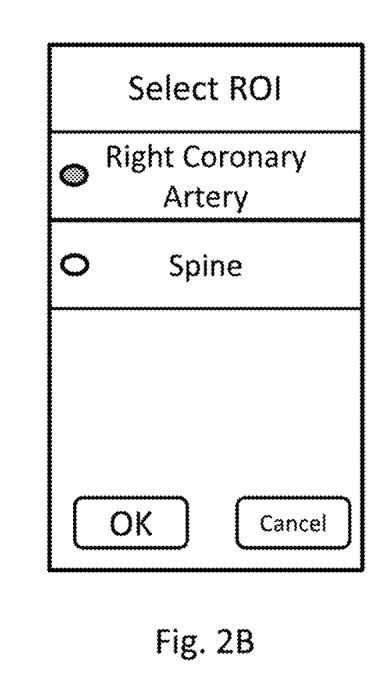

ROIs can be selected by name through a menu (including a drop down menu or a series of radio buttons), see FIGS. 2A and 2B, or the ROIs can be presented on a touchpad and the user can select one.

Figure 3:
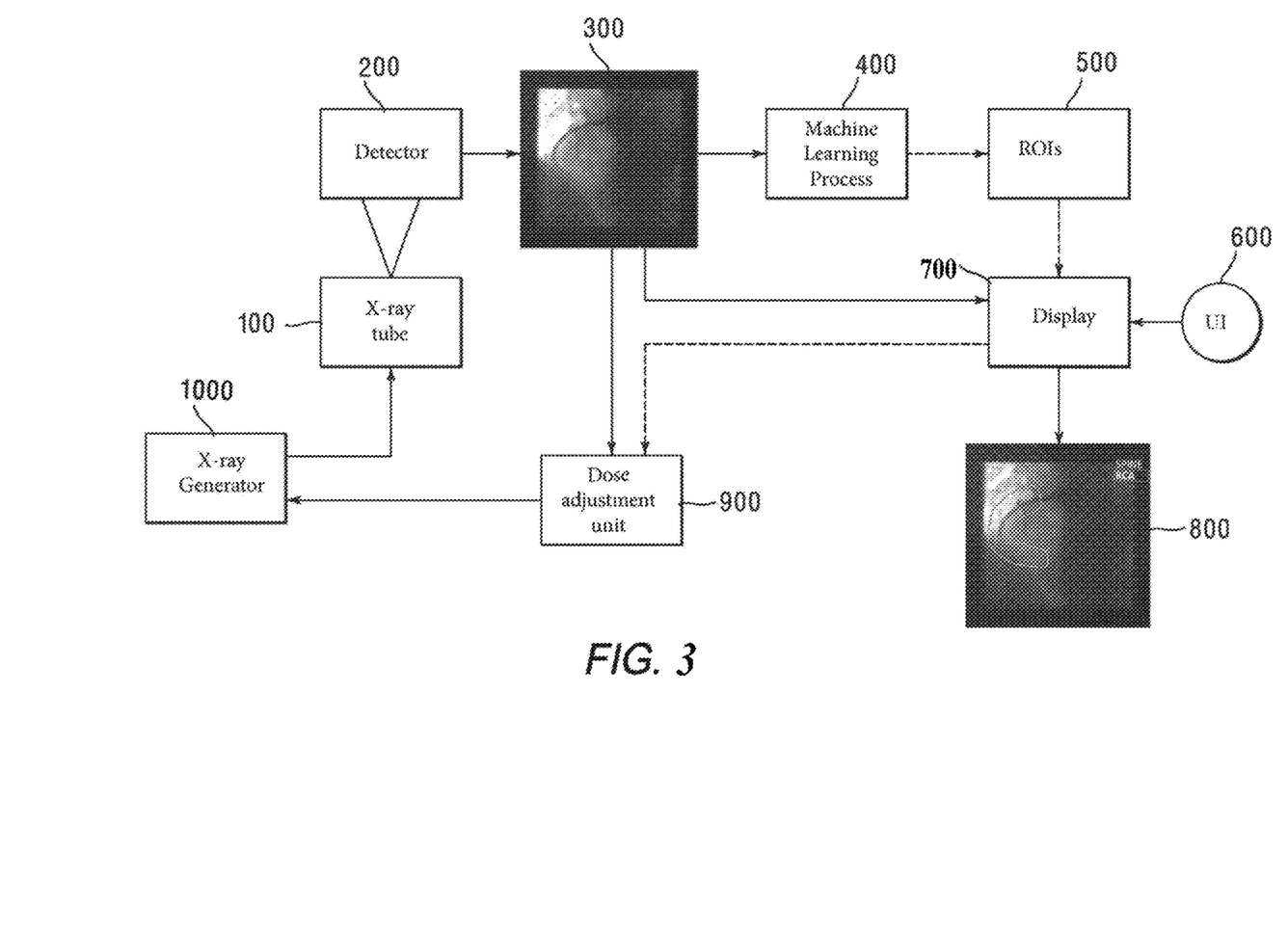
FIG. 3 shows a block diagram indicating the steps in the process of assigning the right x-ray dose to a particular region of interest selected by a user.

FIG. 3 shows a block diagram indicating the steps in one embodiment of a process of assigning the right x-ray dose to a particular ROI selected by the user. In FIG. 3, dashed lines refer to measurement fields, solid lines refer to image data and control information. First, the x-ray tube 100 irradiates an object with x-rays and via a detector 200 an image 300 is displayed. Based on the image 300, an ML process 400 is used to create a list of ROIs and respective measurement fields 500, i.e., outlines of a particular ROI in the image 300. Then, the user, via user interface (UI) 600, selects a measurement field of a particular ROI, and an ROI selection and display unit 700 displays an image 800, where the particular selected ROI is outlined for viewing by the user. After the desired ROI has been selected, its information is provided to a dose adjustment unit 900 that sets the x-ray dose to correspond to the particular ROI and provides the information to the x-ray generator 1000 to irradiate the object with the adjusted x-ray.

Figure 4A:
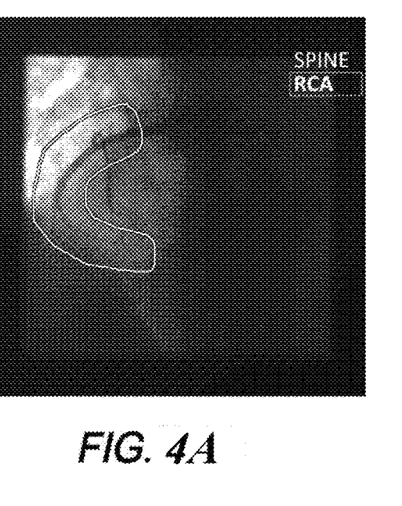
FIGS. 4A and 4B show an x-ray image with selected regions of interest.
Figure 4B:
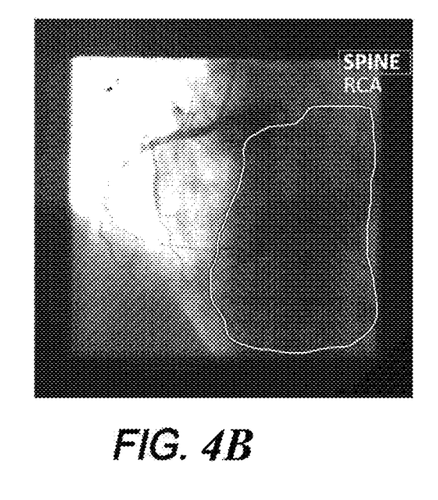

An example of a selection of a particular ROI in an x-ray image is shown in FIGS. 4A and 4B. FIGS. 4A and 4B show x-ray images from the same general region of the body. In FIG. 4A, a measurement field (white outline) corresponding to a particular ROI, i.e., a right coronary artery (RCA), is shown superimposed on the x-ray image. In FIG. 4B, a measurement field (white outline) corresponding to a particular ROI, i.e., the spine, is shown superimposed on the x-ray image. An indicator on the right upper corner of the screen informs the user about the identity of the selected ROI, i.e., RCA or spine. Then, the user selects one ROI, and the dose adjustment unit 900 provides the generator 1000 with the information, so that the generator 1000 selects the x-ray dose appropriate for the selected ROI, i.e., RCA or spine. This produces an x-ray image that has the best visibility for the particular ROI, i.e., RCA (FIG. 3A) or spine (FIG. 3B).

Figure 6:
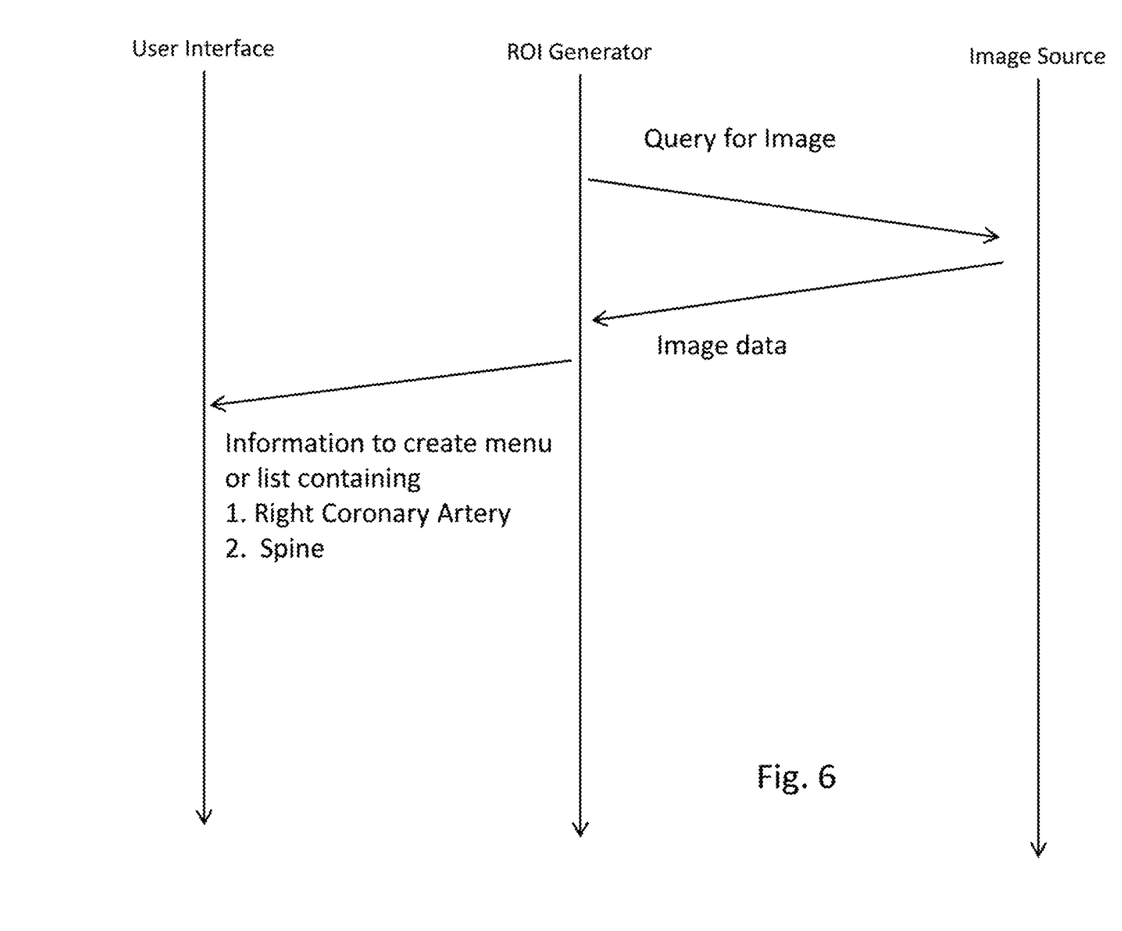
FIG. 6 shows an interface flow-chart in another embodiment.

As seen in the interface flow-chart of FIG. 6, in this embodiment, the ROI generator receives image data from the image source and generates information related to the image, i.e., list of measurement fields. It is noted that the image source may receive a query for an image from the ROI generator.

In another embodiment, a list of objects of interest is created from a configured list of objects expected to be present in the image for the current acquisition. In particular, a list of target objects is selected. This list may be selected by a user from a populated database of medical images of the same or other users in medical records.

Image content can be inferred from, for example, the examination type (e.g., cardiac catheterization, electrophysiology, neuro, abdomen), the patient sex, or prior exam records (e.g., showing device implantation or vessel grafts). The examination type typically infers ROIs according to the following:

Cardiac:
  Coronary arteries
    Right coronary
    Circumflex Artery
    Left Anterior Descending Artery
    Posterior Descending Artery
  Coronary stent
  Catheter
  Guide Wire
  Vertebra
  Diaphragm
Electrophysiology:
  (same as cardiac)
  Ablation Catheter
  Pacemaker
Neuro:
  Carotid Artery
  Cerebral Artery
  Vertebral Artery
  Aneurysm coil
Abdomen:
  Catheter
  Guide Wire
  Aorta
  Ribs
  Diaphragm
  Spine
  Stent
  Renal Artery
  Mesenteric Artery
  Hepatic Artery Then, based on the selected target object, a ROI is detected, via, for example, machine learning, and a measurement field of pixels based on the detected ROI is determined, via, for example, the machine learning process. Finally, based on the determined measurement field, the dose of an x-ray for irradiating the section of the body of the patient corresponding to the selected target object is adjusted.

Figure 5:
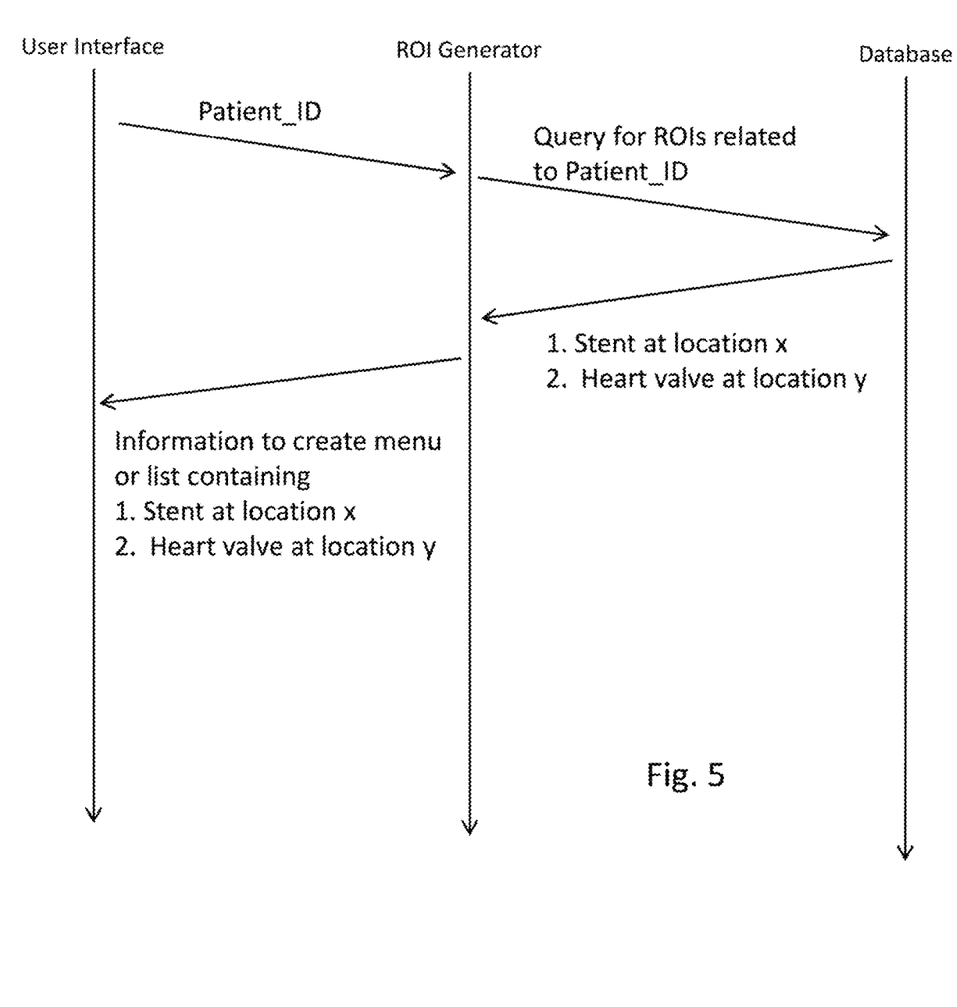
FIG. 5 shows an interface flow-chart in one embodiment.

As seen in the interface flow-chart of FIG. 5, in this embodiment, the user interface provides the ROI generator with user information (e.g., patient identification) and the ROI generator queries the database for ROIs related to the patient ID. Information related to the patient (e.g., a stent located a position x or a heart valve located at a position y) is provided to the ROI generator which generates a list of measurement fields outlining the stent at location x or the heart valve at location y.

The embodiments presented herein may be deployed in angiographic x-ray systems, although other x-ray applications are possible. Connections between components illustrated above may be the same as those existing in current such systems, but could be adapted to other hardware- or software-based connections.

This system advantageously determines regions of interest for x-ray dose adjustment based on image content rather than using histogram analysis of an arbitrary area. In this manner, the x-ray dose can be optimized for visualization of desired objects or regions within the field of view.

Various embodiments discussed herein provide a method for determining and selecting a particular ROI in an x-ray image for adjusting the x-ray dose for the particular ROI.

According to one embodiment, a section of a body of a patient is irradiated to obtain an x-ray image of the section and then a list of ROIs from the x-ray image is created and then a list of measurement fields of pixels corresponding to the created list of ROIs is created and selected, and an x-ray dose for irradiating the section of the body of the patient with an x-ray is adjusted, based on the selected measurement field.

According to one embodiment, the creating a list of ROIs is performed via a machine learning process.

According to another embodiment, the creating a list of ROIs is performed based on predetermined knowledge of the objects present in the x-ray image.

According to still another embodiment, the creating a list of ROIs is performed based on a list of target objects present in medical records and/or selected by a user.

According to one embodiment, the creating a list of measurement fields of pixels is performed based on the machine learning process.

Various embodiments discussed herein provide a system for determining and selecting a particular ROI in an x-ray image for adjusting the x-ray dose for the particular ROI.

According to one embodiment, the system comprises an x-ray tube that irradiates a section of a body of a patient and obtains an x-ray image of the section; and circuitry configured to: create a list of ROIs from the x-ray image; create a list of measurement fields of pixels corresponding to the created list of ROIs; and adjust an x-ray dose for irradiating the section of the body of the patient with an x-ray, based on the selected measurement field.

Embodiments of the present disclosure may also be as set forth in the following parentheticals.

(1) A method for adjusting imaging parameters, the method comprising: imaging irradiating a section of a body of a patient and obtaining an x-ray image of the section; creating a list of regions of interest (ROIs) ROIs related to from the x-ray image; creating a list of measurement fields of pixels corresponding to the created list of ROIs; providing to a user a feedback mechanism for selecting a measurement field from the created list of measurement fields; adjusting determining an x-ray dose for irradiating the section of the body of the patient with an x-ray, based on the selected measurement field; and irradiating the section of the body of the patient with the adjusted determined x-ray dose.

(2) The method of (1), wherein the creating a list of ROIs is performed via a machine learning process.

(3) The method of (1), wherein the creating a list of ROIs is performed based on predetermined knowledge of the objects present in the x-ray image.

(4) The method of any one of (1) to (3), wherein the list of ROIs is presented concurrently with the x-ray image, along with indications as to the ROI currently being used to establish the measurement field for dose adjustment.

(5) The method of any one of (1) to (4), wherein the measurement fields corresponding to particular ROIs are indicated on the x-ray image, either temporarily or persistently.

(6) The method any one of (1) to (5), wherein the user changes the a selection of a current ROI using an input device including, a mouse, a joystick, a jog wheel, a touch panel, or voice control.

(7) The method of (2), wherein the machine learning process is an object detection, localization, segmentation, or tracking process.

(8) The method of (2), wherein the creating a list of measurement fields of pixels is performed based on the machine learning process.

(9) The method of (6), wherein upon selection of a new ROI by the user, the method further comprising determining a new corresponding measurement field, for determining the new x-ray adjustment determination.

(10) The method of (4), wherein ROIs are selected by name via a menu.

(11) The method of any one of (1) to (10), wherein the dimensions of the measurement fields of pixels corresponding to particular ROIs are based on the type of objects present in the particular ROIs.

(12) The method of any one of (1) to (11), wherein the imaging a section of the body of the patient comprises irradiating the section and obtaining an x-ray image of the section.

(13) A system for determining and selecting a particular region of interest (ROI) in an x-ray image, for adjusting the x-ray dose for the particular ROI, the system comprising: an x-ray tube that irradiates a section of a body of a patient and obtains an x-ray image of the section; and circuitry configured to: create a list of ROIs from related to the x-ray image; create a list of measurement fields of pixels corresponding to the created list of ROIs; provide to a user a feedback mechanism for selecting a measurement field from the created list of measurement fields; and adjust an x-ray dose for irradiating the section of the body of the patient with an x-ray, based on the selected measurement field, wherein the x-ray tube irradiates the section of the body of the patient with the adjusted x-ray dose.

(14) The system of (13), wherein the circuitry performs the creating a list of ROIs via a machine learning process.

(15) The system of (13), wherein the circuitry performs the creating a list of ROIs based on predetermined knowledge of the objects present in the x-ray image.

(16) The system of any one of (13) to (15), wherein the list of ROIs is presented concurrently with the x-ray image, along with indications as to the ROI currently being used to establish the measurement field for dose adjustment.

(17) The system of any one of (13) to (16), wherein the measurement fields corresponding to particular ROIs are indicated on the x-ray image, either temporarily or persistently.

(18) The system of any one of (13) to (17), wherein the user changes the selection of a current ROI using an input device including, a mouse, a joystick, a jog wheel, a touch panel, or voice control.

(19) The system of (14), wherein the machine learning process is an object detection, localization, segmentation, or tracking process.

(20) The system of (14), wherein the circuitry performs the creating a list of measurement fields of based on the machine learning process.

(21) The system of (16), wherein upon selection of a new ROI by the user, the circuitry further determines a new corresponding measurement field, for determining the new x-ray adjustment.

(22) The system of (16), wherein ROIs are selected by name via a menu.

(23) A method for determining and selecting a particular region of interest (ROI) in an x-ray image for adjusting the x-ray dose for the particular ROI adjusting imaging parameters, the method comprising: accepting an operation of selecting a target object; irradiating imaging a section of a body of a patient and obtaining an x-ray image of the section; detecting determining a region of interest (ROI) corresponding to the target object from related to the obtained x-ray image; creating a measurement field of pixels based on the detected ROI; adjusting determining an x-ray dose for irradiating the section of the body of the patient with an x-ray, based on the created measurement field; and irradiating the section of the body of the patient with the adjusted determined x-ray dose.

(24) The method of (23), wherein a list of ROIs is presented concurrently with the x-ray image, along with indications as to the ROI currently being used to establish the measurement field for dose adjustment determination.

(25) The method of either (23) or (24), wherein the measurement fields corresponding to particular ROIs are indicated on the x-ray image, either temporarily or persistently.

(26) The method of any one of (23) to (25), wherein a user changes a selection of a current ROI using an input device including, a mouse, a joystick, a jog wheel, a touch panel, or voice control.

(27) The method of (26), wherein upon selection of a new ROI by the user, the method further comprising determining a new corresponding measurement field, for determining the new x-ray adjustment.

(28) The method of (24), wherein ROIs are selected by name via a menu.

(29) The method of (23), wherein the target object is selected by a user and/or selected from medical records.

(30) The method of (23), wherein the adjusting determining an x-ray dose is further based on the selected target object associated with the created measurement field.

(31) The method of (23), wherein the detecting an ROI is performed via a machine learning process.

(32) The method of (31), wherein the creating of a measurement field of pixels is performed based on the machine learning process.

(33) The method of (23), wherein the dimensions of the measurement fields of pixels corresponding to particular ROIs are based on the type of objects present in the particular ROIs.

(34) The method of (23), wherein the imaging a section of the body of the patient comprises irradiating the section and obtaining an x-ray image of the section.

Numerous modifications and variations of the embodiments presented herein are possible in light of the above teachings. It is therefore to be understood that within the scope of the claims, the disclosure may be practiced otherwise than as specifically described herein.

The invention claimed is:

1. A method for adjusting imaging parameters, the method comprising:
   imaging a section of a body including objects of a patient and obtaining an x-ray image of the section;
   creating a list of regions of interest (ROIs) corresponding to the objects captured in the x-ray image;
   creating a list of measurement fields of pixels corresponding to the created list of ROIs;
   providing to a user a feedback mechanism for selecting a measurement field corresponding to an ROI;
   determining an x-ray dose for irradiating the section of the body of the patient with an x-ray, based on the measurement field corresponding to a selection of the ROI; and
   irradiating the section of the body of the patient with the determined x-ray dose.

2. The method according to claim 1, wherein the creating a list of ROIs is performed by creating a list of image content of the x-ray image via a machine learning process.

3. The method according to claim 2, wherein the machine learning process is an object detection, localization, segmentation, or tracking process.

4. The method according to claim 2, wherein the creating a list of measurement fields of pixels is performed based on the machine learning process.

5. The method according to claim 1, wherein the creating a list of ROIs is performed by creating a list of image content of the x-ray image based on predetermined knowledge of the objects present in the x-ray image.

6. The method according to claim 1, wherein the list of ROIs is presented concurrently with the x-ray image, along with indications as to the ROI currently being used to establish the measurement field for dose adjustment.

7. The method according to claim 6, wherein ROIs are selected by name via a menu.

8. The method according to claim 1, wherein the measurement fields corresponding to particular ROIs are indicated on the x-ray image, either temporarily or persistently.

9. The method according to claim 1, wherein the user changes a selection of a current ROI using an input device including, a mouse, a joystick, a jog wheel, a touch panel, or voice control.

10. The method according to claim 9, wherein upon selection of a new ROI by the user, the method further comprising determining a new corresponding measurement field, for a new determination of the x-ray dose based on the new corresponding measurement field.

11. The method according to claim 1, wherein dimensions of measurement fields of pixels corresponding to particular ROIs are based on a type of objects present in the particular ROIs.

12. The method according to claim 1, wherein the imaging a section of the body of the patient comprises irradiating the section and obtaining the x-ray image of the section.

13. The method according to claim 1, wherein a shape of the measurement field corresponds to a shape of the ROI.

14. The method according to claim 1, wherein a shape of the measurement field corresponds to an outline of the ROI.

15. The method according to claim 1, wherein the measurement field is formed by adding a predetermined margin to an outline of the ROI.

16. The method according to claim 1, wherein the creating a list of ROIs comprises accepting an operation of selecting a particular list from a plurality of lists stored by a memory and causing objects included in the selected particular list and captured in the x-ray image to be included in the list of ROIs, the memory storing, for each protocol for obtaining the x-ray image, a list of objects expected to be present in the x-ray image.

17. A system for determining and selecting a particular region of interest (ROI) in an x-ray image, for adjusting an x-ray dose for the particular ROI, the system comprising:

an x-ray tube that irradiates a section of a body including objects of a patient and obtains an x-ray image of the section; and circuitry configured to:
create a list of ROIs corresponding to the objects captured in the x-ray image;
create a list of measurement fields of pixels corresponding to the created list of ROIs;
provide to a user a feedback mechanism for selecting a measurement field corresponding to an ROI; and
adjust an x-ray dose for irradiating the section of the body of the patient with an x-ray, based on the measurement field corresponding to a selection of the ROI, wherein
the x-ray tube irradiates the section of the body of the patient with the adjusted x-ray dose.

18. The system according to claim 17, wherein the circuitry performs the creating a list of ROIs by creating a list of image content of the x-ray image via a machine learning process.

19. The system according to claim 17, wherein the circuitry performs the creating a list of ROIs by creating a list of image content of the x-ray image based on predetermined knowledge of the objects present in the x-ray image.

20. A method for adjusting imaging parameters, the method comprising:
accepting an operation of selecting a target object;
imaging a section of a body of a patient and obtaining an x-ray image of the section;
determining a region of interest (ROI) corresponding to the target object captured in the obtained x-ray image related to the obtained x-ray image;
creating a measurement field of pixels based on the determined ROI;
determining an x-ray dose for irradiating the section of the body of the patient with an x-ray, based on the created measurement field; and
irradiating the section of the body of the patient with the determined x-ray dose.

21. The method according to claim 20, wherein the determining an x-ray dose is further based on the selected target object associated with the created measurement field.

22. The method according to claim 20, wherein the determining an ROI is performed via a machine learning process.

23. The method according to claim 22, wherein the creating of a measurement field of pixels is performed based on the machine learning process.

24. The method according to claim 20, wherein dimensions of measurement fields of pixels corresponding to particular ROIs are based on a type of objects present in the particular ROIs.

* * * * *